US008659647B2

(12) United States Patent
 Segawa

(10) Patent No.: US 8,659,647 B2
(45) Date of Patent: Feb. 25, 2014

(54) IMAGE PICKUP DEVICE AND IMAGE PICKUP SYSTEM WITH BIT VALUE INVERSION

(71) Applicant: Olympus Medical Systems Corp., Tokyo (JP)

(72) Inventor: Kazunori Segawa, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/774,179

(22) Filed: Feb. 22, 2013

(65) Prior Publication Data

US 2013/0235173 A1  Sep. 12, 2013

Related U.S. Application Data

(63) Continuation of application No. PCT/JP2012/070340, filed on Aug. 9, 2012.

(30) Foreign Application Priority Data

Aug. 26, 2011  (JP) ................................. 2011-185129

(51) Int. Cl.
 *H04N 7/18*  (2006.01)
(52) U.S. Cl.
 USPC ........................................................ 348/65
(58) Field of Classification Search
 USPC ........................................................ 348/65
 IPC ..................................................... H04N 7/18
 See application file for complete search history.

(56) References Cited

U.S. PATENT DOCUMENTS

2009/0160973 A1 * 6/2009 Houda et al. ............... 348/231.2

FOREIGN PATENT DOCUMENTS

| JP | 63-042548 | 2/1988 |
| JP | 2007-167590 | 7/2007 |
| WO | 97/13348 A2 | 4/1997 |

OTHER PUBLICATIONS

Extended Supplementary European Search Report dated Oct. 31, 2013 from related European Application No. 12 82 7667.2.

* cited by examiner

*Primary Examiner* — Jay Patel
*Assistant Examiner* — Yulin Sun
(74) *Attorney, Agent, or Firm* — Scully, Scott, Murphy & Presser, P.C.

(57) ABSTRACT

An image pickup apparatus includes an image pickup section that acquires an image by image pickup of an object and acquire digital data of the image, a determining section that determines whether there are a predetermined number or more of consecutive bits with a first bit value or a second bit value in data per pixel included in the digital data, a bit value inversion processing section that inverts, when a determination result that there are the predetermined number or more of consecutive bits with the first or the second bit value is obtained, the bit values so that a ratio between the first bit value and the second bit value included in the corresponding pixel data becomes a predetermined ratio, and a serial conversion section that serializes and outputs the respective bit values of the digital data obtained as the processing result of the bit value inversion processing section.

6 Claims, 3 Drawing Sheets

| 3-BIT DATA | 4-BIT DATA |
| --- | --- |
| 000 | (A)0100/(B)1011 |
| 001 | 0011 |
| 010 | 0101 |
| 011 | 0110 |
| 100 | 1001 |
| 101 | 1010 |
| 110 | 1100 |
| 111 | (A)0010/(B)1101 |

IMAGE PICKUP DEVICE AND IMAGE PICKUP SYSTEM WITH BIT VALUE INVERSION

CROSS REFERENCE TO RELATED APPLICATION

This application is a continuation application of PCT/JP2012/070340 filed on Aug. 9, 2012 and claims benefit of Japanese Application No. 2011-185129 filed in Japan on Aug. 26, 2011, the entire contents of which are incorporated herein by this reference.

BACKGROUND OF THE INVENTION

1. Field of the Invention

The present invention relates to an image pickup system, and more particularly, to an image pickup apparatus and an image pickup system capable of serially transmitting digital data of an image acquired by image pickup of an object.

2. Description of the Related Art

As a transmission scheme for serially transmitting digital data of an image acquired by image pickup of an object using an image pickup apparatus such as an endoscope, a differential transmission scheme such as an LVDS (low voltage differential signaling) scheme is conventionally used, which is disclosed, for example, in Japanese Patent Application Laid-Open Publication No. 2007-167590.

To be more specific, Japanese Patent Application Laid-Open Publication No. 2007-167590 discloses an endoscope apparatus having a configuration that converts a video signal from an endoscope to digital parallel signals, generates, from respective bits of the parallel signals, a bit data set that combines bit data per bit and inverted data of the bit data, converts the bit data set to serial data and transmits the serial data using the LVDS scheme.

SUMMARY OF THE INVENTION

An image pickup apparatus according to an aspect of the present invention includes an image pickup section configured to acquire an image by image pickup of an object and acquire digital data of the image, a determining section that determines whether or not there are a predetermined number or more of consecutive bits with a first bit value or a second bit value in data per pixel included in the digital data acquired by the image pickup section, a bit value inversion processing section that applies, when a determination result that there are the predetermined number or more of consecutive bits with the first bit value or the second bit value is obtained from the determining section, processing of inverting the bit values so that a ratio between the first bit value and the second bit value included in the pixel data corresponding to the determination result becomes a predetermined ratio to the digital data acquired by the image pickup section, and a serial conversion section that serializes and outputs the respective bit values of the digital data obtained as the processing result of the bit value inversion processing section.

An image pickup system according to an aspect of the present invention includes an image pickup section configured to acquire an image by image pickup of an object and acquire digital data of the image, a determining section that determines whether or not there are a predetermined number or more of consecutive bits with a first bit value or a second bit value in data per pixel included in the digital data acquired by the image pickup section, a bit value inversion processing section that applies, when a determination result that there are the predetermined number or more of consecutive bits with the first bit value or the second bit value is obtained from the determining section, processing of inverting the bit values so that a ratio between the first bit value and the second bit value included in the pixel data corresponding to the determination result becomes a predetermined ratio to the digital data acquired by the image pickup section, a serial conversion section that serializes and outputs the respective bit values of the digital data obtained as the processing result of the bit value inversion processing section, a digital data transmission section that transmits the digital data serialized by the serial conversion section, a digital data reception section that receives the digital data transmitted from the digital data transmission section, a parallel conversion section that converts the digital data received from the digital data reception section to parallel data, and a bit value re-inversion processing section that applies, when a determination result that there are the predetermined number or more of consecutive bits with the first bit value or the second bit value is obtained from the determining section, processing of re-inverting the respective bit values inverted by the processing in the bit value inversion processing section to the parallel data obtained as the conversion result in the parallel conversion section.

DETAILED DESCRIPTION OF THE PREFERRED EMBODIMENT

Hereinafter, an embodiment of the present invention will be described with reference to the accompanying drawings.

Figure 1:
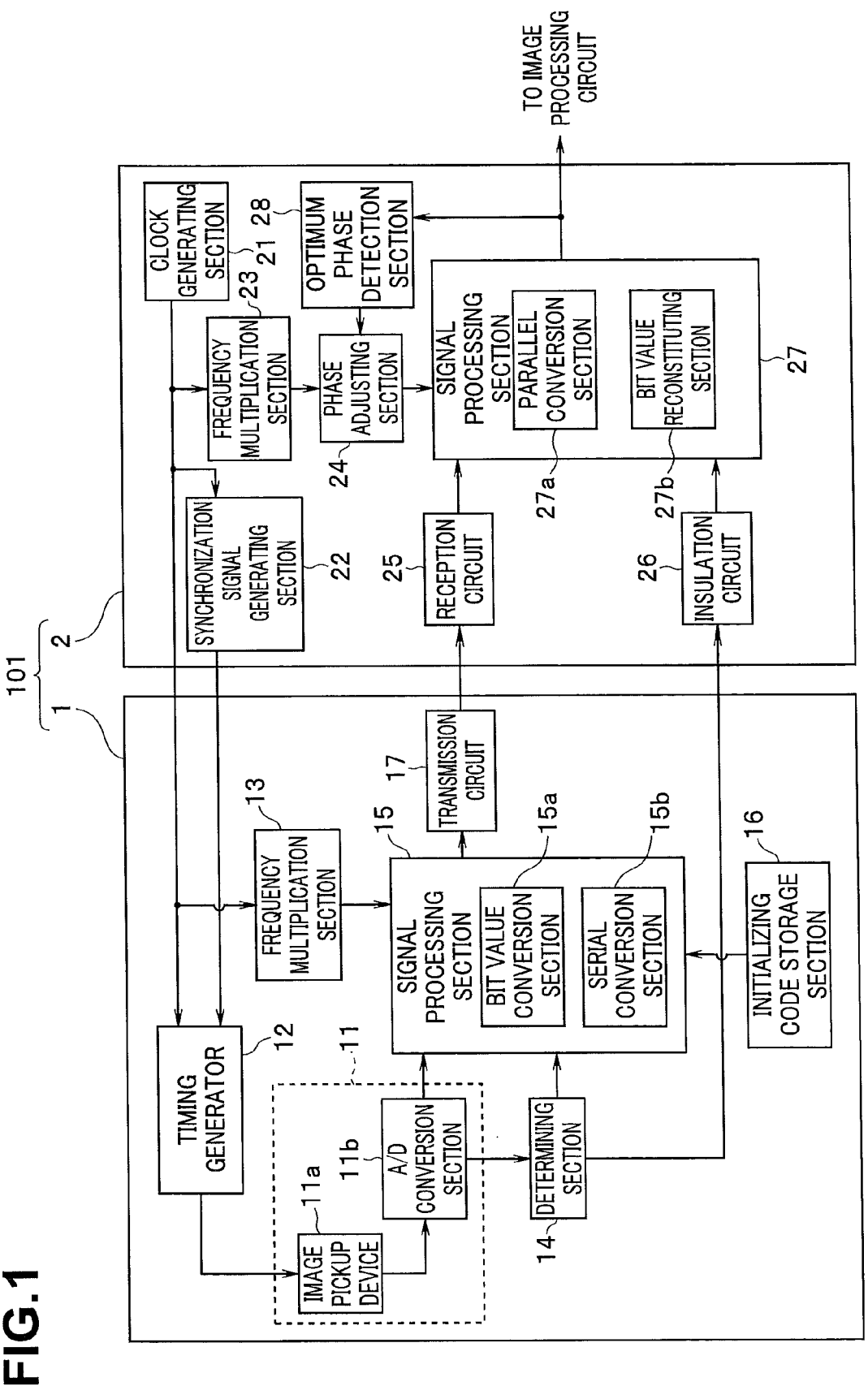
FIG. 1 is a block diagram illustrating a configuration of principal components of an image pickup system including an image pickup apparatus according to an embodiment of the present invention.

FIG. 1 to FIG. 5 relate to an embodiment of the present invention. FIG. 1 is a block diagram illustrating a configuration of principal components of an image pickup system including an image pickup apparatus according to an embodiment of the present invention.

As shown in FIG. 1, an image pickup system 101 includes an image pickup apparatus 1 configured by including a camera head of a video scope or rigid endoscope and the like, and a camera control unit (hereinafter, referred to as "CCU") 2 that exchanges various signals and data with the image pickup apparatus 1.

The image pickup apparatus 1 is configured by including an image pickup section 11, a timing generator 12, a frequency multiplication section 13, a determining section 14, a signal processing section 15, an initializing code storage section 16 and a transmission circuit 17.

The image pickup section 11 is configured by including an image pickup device 11a made up of a CCD or the like and an A/D conversion section 11b.

The image pickup device 11a is configured to be driven by an HD (horizontal drive) signal and a VD (vertical drive) signal supplied from the timing generator 12, photoelectrically convert (pick up an image of) an object image formed on a light-receiving surface by an optical system (not shown) and output (acquire an image) an analog image pickup signal.

The A/D conversion section 11b is configured to sample the image pickup signal outputted from the image pickup device 11a at every predetermined period, thereby convert a signal level of each pixel of the image pickup signal to digital data with a predetermined number of bits with bit values of 0 or 1 and output the digital data.

In other words, the image pickup section 11 is configured to be able to acquire an image by image pickup of an object and acquire digital data of the image.

The timing generator 12 generates and outputs an HD signal and a VD signal to define drive timing of the image pickup device 11a based on a clock signal and a synchronization signal supplied from the CCU 2.

The frequency multiplication section 13 is configured by including an error detection function that can detect an error of the clock signal supplied from the CCU 2. The frequency multiplication section 13 then resets the clock signal based on the error detection result by the error detection function, multiplies the frequency of the reset clock signal N-fold (e.g., four-fold) and outputs the clock signal to the signal processing section 15.

The determining section 14 determines whether or not the digital data outputted from the A/D conversion section 11b corresponds to a predetermined condition (which will be described later), generates a determination signal corresponding to the determination result and outputs the determination signal to the signal processing section 15 and the CCU 2.

The (each section of) signal processing section 15 is configured to be able to operate based on the clock signal outputted from the frequency multiplication section 13. Furthermore, the signal processing section 15 is configured by including a bit value conversion section 15a and a serial conversion section 15b.

The bit value conversion section 15a provided with a function as a bit value inversion processing section converts a bit value of digital data outputted from the A/D conversion section 11b according to a predetermined pattern (which will be described later) based on the determination signal outputted from the determining section 14 for a period corresponding to an effective period of the image pickup device 11a.

Furthermore, the bit value conversion section 15a converts (substitutes) the bit value of the digital data outputted from the A/D conversion section 11b to a bit value corresponding to a fixed code stored beforehand in the initializing code storage section 16 for a period corresponding to a blanking period (vertical blanking period; the same shall apply hereinafter) of the image pickup device 11a. Note that the conversion (substitution) processing of the bit value using such a fixed code will be described later with additional information.

The serial conversion section 15b is configured by including a serializer or the like, and configured to serialize each bit value of the digital data obtained as the processing result of the bit value conversion section 15a and output the serialized bit value to the transmission circuit 17.

The initializing code storage section 16 stores fixed code data set beforehand for each image pickup apparatus 1 as the data used to establish synchronization in operation between the image pickup apparatus 1 and the CCU 2 so as not to affect EMI (electro magnet interference) of a signal (differential transmission signal) transmitted from the transmission circuit 17.

The transmission circuit 17 provided with a function as a digital data transmission section is configured by including a buffer or the like, and configured to convert the digital data outputted from the signal processing section 15 to a differential transmission signal corresponding to a predetermined scheme such as an LVDS scheme and transmit the differential transmission signal to the CCU 2.

On the other hand, the CCU 2 is configured by including a clock generating section 21, a synchronization signal generating section 22, a frequency multiplication section 23, a phase adjusting section 24, a reception circuit 25, an insulation circuit 26, a signal processing section 27, and an optimum phase detection section 28.

The clock generating section 21 generates a clock signal having a predetermined frequency to be used for operation of each section of the image pickup apparatus 1 and the CCU 2 and outputs the clock signal to the image pickup apparatus 1 and the synchronization signal generating section 22.

The synchronization signal generating section 22 generates a synchronization signal used to generate an HD signal and a VD signal based on the clock signal supplied from the clock generating section 21 and outputs the synchronization signal to the image pickup apparatus 1.

The frequency multiplication section 23 multiplies the frequency of the clock signal supplied from the clock generating section 21 N-fold (e.g., four-fold) and outputs the clock signal to the phase adjusting section 24.

The phase adjusting section 24 adjusts the phase of the clock signal frequency-multiplied by the frequency multiplication section 23 based on a detection result of the optimum phase detection section 28 and outputs the adjusted clock signal to the signal processing section 27.

The reception circuit 25 provided with a function as a digital data reception section is configured by including a pulse transformer or the like, and configured to receive the differential transmission signal transmitted from the image pickup apparatus 1, generate digital data corresponding to the received differential transmission signal and output the digital data to the signal processing section 27.

The insulation circuit 26 is configured to be able to receive the determination signal transmitted from the image pickup apparatus 1 while remaining electrically insulated from the image pickup apparatus 1.

The (each section of) signal processing section 27 is configured to be able to operate based on the clock signal outputted from the phase adjusting section 24. Furthermore, the signal processing section 27 is configured by including a parallel conversion section 27a and a bit value reconstituting section 27b.

The parallel conversion section 27a is configured by including a deserializer or the like, and configured to convert each serialized bit value included in the digital data outputted from the reception circuit 25 to parallel data.

For a period corresponding to an effective period of the image pickup device 11a, the bit value reconstituting section 27b provided with a function as a bit value re-inversion processing section re-converts bit values of the parallel data obtained through the processing of the parallel conversion section 27a according to the same pattern as a conversion pattern of the bit value conversion section 15a based on the determination signal outputted from the insulation circuit 26, thereby reconstitutes the data before being transmitted from the transmission circuit 17 and outputs the reconstituted data to an image processing circuit (not shown) positioned after the CCU 2.

For a period corresponding to the blanking period of the image pickup device 11a, the bit value reconstituting section 27b extracts data corresponding to the fixed code stored in the initializing code storage section 16 from the parallel data obtained through the processing of the parallel conversion section 27a and outputs the data to the optimum phase detection section 28.

Based on the data extraction result by the bit value reconstituting section 27b, the optimum phase detection section 28 detects a phase that allows each serialized bit value outputted from the reception circuit 25 to be latched at most suitable timing when the parallel conversion section 27a generates parallel data. Note that such phase detection processing will be described later with additional information.

Next, operation or the like of the image pickup system 101 of the present embodiment will be described. Note that a case will be described hereinafter where 16-bit data is generated as one pixel worth of data as an example, unless specified otherwise. First, when power is supplied to each component of the image pickup system 101, a clock signal generated by the clock generating section 21 and a synchronization signal generated by the synchronization signal generating section 22 are supplied to the timing generator 12.

The timing generator 12 generates an HD signal and a VD signal to define drive timing of the image pickup device 11 a based on the clock signal and the synchronization signal supplied from the CCU 2 and outputs those signals.

The image pickup device 11a is driven according to the HD (horizontal drive) signal and the VD (vertical drive) signal supplied from the timing generator 12, thereby picks up an object image and outputs an analog image pickup signal.

The A/D conversion section 11b samples the image pickup signal outputted from the image pickup device 11a at every predetermined period, thereby converts a signal level of each pixel of the image pickup signal to 16-bit digital data and outputs the digital data.

The determining section 14 determines a light-shielded pixel or saturated pixel based on the data per pixel included in the digital data outputted from the A/D conversion section 11b, generates a determination signal corresponding to the determination result and outputs the determination signal to the signal processing section 15 and the CCU 2.

To be more specific, upon detecting that there are a predetermined number or more of consecutive bits with bit values of 0 among 16 bits (e.g., 8 bits which is half of 16 bits) in one pixel worth of data based on data per pixel included in the digital data outputted from the A/D conversion section 11b, the determining section 14 obtains a determination result that the one pixel worth of data is obtained from the light-shielded pixel.

Furthermore, upon detecting that there are a predetermined number or more of consecutive bits with bit values of 1 among 16 bits (e.g., 8 bits which is half of 16 bits) in one pixel worth of data based on data per pixel included in the digital data outputted from the A/D conversion section 11b, the determining section 14 obtains a determination result that the one pixel worth of data is obtained from the saturated pixel.

Furthermore, upon detecting that, for example, there are not a predetermined number or more of consecutive bits with bit values of 0 or 1 among 16 bits (e.g., 8 bits) in one pixel worth of data based on data per pixel included in the digital data outputted from the A/D conversion section 11b, the determining section 14 obtains a determination result that the one pixel worth of data is obtained from the neither light-shielded nor saturated pixel.

Based on the determination signal outputted from the determining section 14, the bit value conversion section 15a performs processing of inverting bit values for a period corresponding to an effective period of the image pickup device 11a so that the ratio of bit values of 0 and 1 becomes a predetermined ratio in the data of the pixel which is determined to be a light-shielded pixel or saturated pixel out of the data per pixel included in the digital data outputted from the A/D conversion section 11b.

Figure 2:
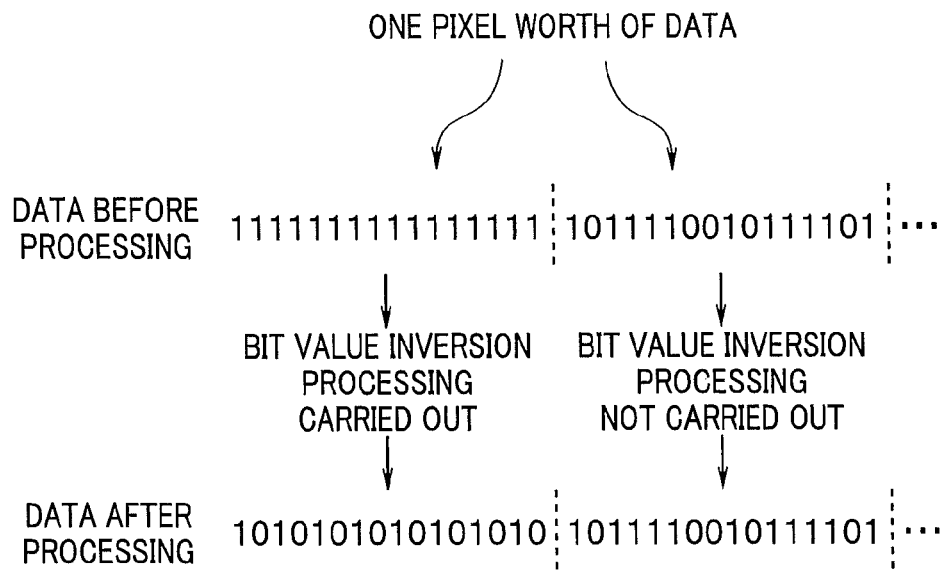
FIG. 2 is a diagram illustrating an example of processing carried out in a bit value conversion section.

FIG. 2 is a diagram illustrating an example of processing carried out in the bit value conversion section.

To be more specific, the bit value conversion section 15a performs processing of inverting bit values so that the ratio of bit values of 0 and 1 in one pixel worth of data determined to be, for example, a light-shielded pixel or saturated pixel becomes 1:1. By performing such processing, there are 8 bits with bit values of 0 and 8 bits with bit values of 1 in the one pixel worth of data of 16 bits determined to be a saturated pixel like "1111111111111111" in FIG. 2, for example. Furthermore, by performing the aforementioned processing, there are 8 bits with bit values of 0 and 8 bits with bit values 1 in the one pixel worth of data of 16 bits determined to be a light-shielded pixel like "0000000000000000," for example.

Note that as long as the bit value conversion section 15a inverts bit values so that the ratio of bit values of 0 and 1 in the data of the pixel determined to be a light-shielded pixel or saturated pixel becomes a predetermined ratio, the bit value conversion section 15a may invert bit values, for example, on a bit-by-bit basis, or may invert bit values in other patterns.

On the other hand, the bit value conversion section 15a does not perform the aforementioned processing of inverting bit values on data of a pixel determined to be neither light-shielded nor saturated pixel out of the data per pixel included in the digital data outputted from the A/D conversion section 11b based on the determination signal outputted from the determining section 14 (see FIG. 2).

Figure 3:
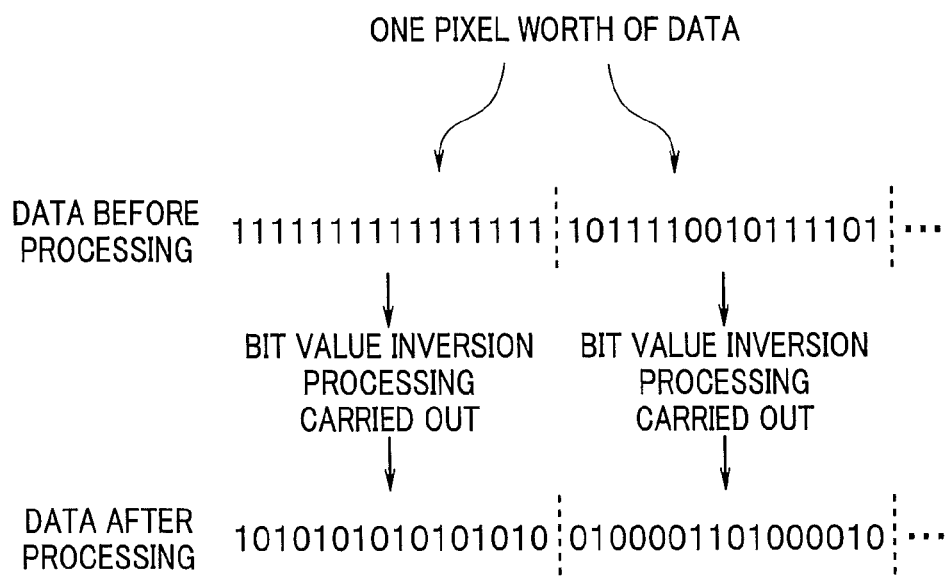
FIG. 3 is a diagram different from FIG. 2, illustrating an example of the processing carried out in the bit value conversion section.

FIG. 3 is a diagram different from FIG. 2, illustrating an example of processing carried out in the bit value conversion section.

Note that the bit value conversion section 15a of the present embodiment is not limited to one that determines whether or not to perform processing of inverting bit values on data per pixel included in the digital data outputted from the A/D conversion section 11b according to the determination result included in the determination signal outputted from the determining section 14, but may also be one that always performs processing of inverting bit values of data per pixel included in the digital data outputted from the A/D conversion section 11b, regardless of the determination result included in the determination signal outputted from the determining section 14 on a bit-by-bit basis as shown, for example, in FIG. 3.

On the other hand, for a period corresponding to a blanking period of the image pickup device 11a, the bit value conversion section 15a converts (substitutes) bit values of the digital data outputted from the A/D conversion section 11b to bit values corresponding to a fixed code stored beforehand in the initializing code storage section 16.

To be more specific, when, for example, the fixed code stored beforehand in the initializing code storage section 16 is data expressed as "A55A" in hexadecimal, the bit value conversion section 15a converts the fixed code to binary data of "1010010101011010."

Then, the bit value conversion section 15a converts (substitutes) bit values of data per pixel included in the digital data outputted from the A/D conversion section 11*b* to bit values of binary data corresponding to the aforementioned fixed code for a period corresponding to the blanking period of the image pickup device 11*a*.

Note that the aforementioned processing of embedding the fixed code for a period corresponding to the blanking period of the image pickup device 11*a* may be performed at every blanking period or may be performed intermittently to an extent that does not affect EMI.

The digital data obtained as the processing result of the bit value conversion section 15*a* is serialized by the serial conversion section 15*b*, converted to a differential transmission signal by the transmission circuit 17, differentially transmitted and then received by the reception circuit 25.

The reception circuit 25 is configured by including a pulse transformer or the like, and configured to receive the differential transmission signal transmitted from the image pickup apparatus 1, generate digital data corresponding to the received differential transmission signal and output the digital data to the signal processing section 27.

The parallel conversion section 27*a* converts each serialized bit value included in the digital data outputted from the reception circuit 25 to parallel data.

Based on the determination signal outputted from the insulation circuit 26, the bit value reconstituting section 27*b* re-inverts bit values of 0 and 1 in the data of the pixel determined to be a light-shielded pixel or saturated pixel out of data per pixel included in the parallel data obtained through the processing in the parallel conversion section 27*a* according to the same pattern as the inverted pattern of the bit value conversion section 15*a*, and thereby performs processing of reconstituting the data before being transmitted from the transmission circuit 17 for a period corresponding to an effective period of the image pickup device 11*a*.

To be more specific, if, for example, the bit value conversion section 15*a* has set a pattern in which bit values of data of a light-shielded pixel or saturated pixel are inverted on a bit-by-bit basis, the bit value reconstituting section 27*b* re-inverts each bit value inverted according to the pattern (on a bit-by-bit basis) and thereby reconstitutes the data before being transmitted from the transmission circuit 17.

The bit value reconstituting section 27*b* then outputs the data reconstituted by the aforementioned processing to an image processing circuit (not shown) positioned after the CCU 2 for a period corresponding to the effective period of the image pickup device 11*a*.

On the other hand, the bit value reconstituting section 27*b* extracts data corresponding to the fixed code stored in the initializing code storage section 16 from the parallel data obtained through the processing of the parallel conversion section 27*a* and outputs the data to the optimum phase detection section 28 for a period corresponding to the blanking period of the image pickup device 11*a*.

Based on the data extraction result by the bit value reconstituting section 27*b*, the optimum phase detection section 28 detects a phase (optimum clock phase) that allows each serialized bit value outputted from the reception circuit 25 to be latched at optimum timing when generating parallel data in the parallel conversion section 27*a*.

Figures 4, 5:
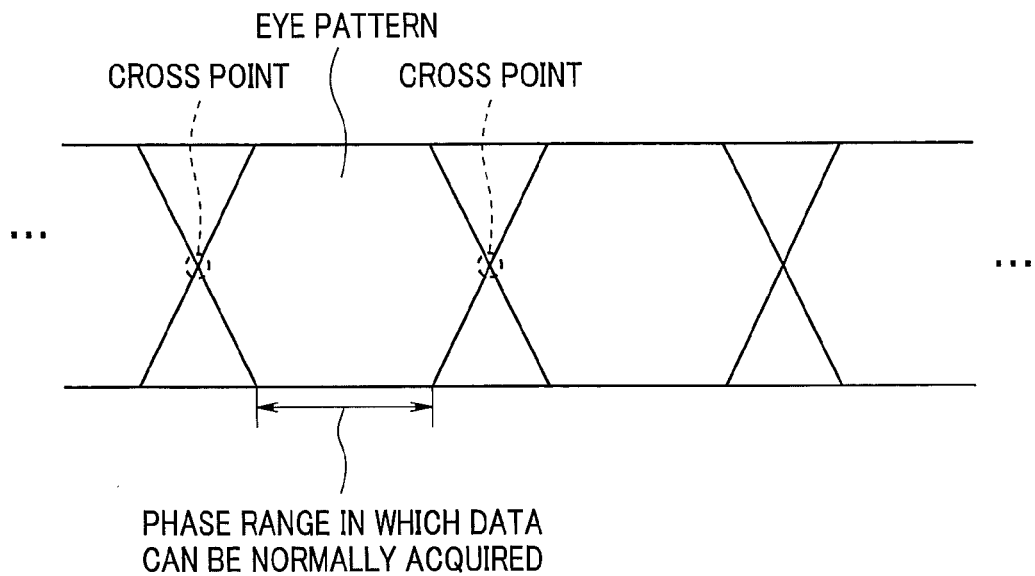
FIG. 4 is a diagram illustrating processing carried out in an optimum phase detection section.
FIG. 5 is a diagram illustrating an example of table data used in processing according to a modification example of the present embodiment.

FIG. 4 is a diagram illustrating processing carried out in the optimum phase detection section.

To be more specific, based on the data extraction result by the bit value reconstituting section 27*b*, the optimum phase detection section 28 detects the portion of data of mutually adjacent bit values except the vicinity of a cross point of an eye pattern as shown, for example, in FIG. 4 as a phase range in which data corresponding to the fixed code stored in the initializing code storage section 16 can be normally acquired. The optimum phase detection section 28 then detects a phase in the center of the phase range detected as described above as a phase (optimum clock phase) at which each serialized bit value outputted from the reception circuit 25 can be latched at optimum timing.

The phase adjusting section 24 then shifts the phase of the clock signal multiplied by the frequency multiplication section 23 so as to be a phase (optimum clock phase) in accordance with the detection result of the optimum phase detection section 28 and outputs the shifted phase to the signal processing section 27.

That is, according to the aforementioned processing in the optimum phase detection section 28 or the like, latch timing in the parallel conversion section 27*a* is adjusted to optimum timing using the data corresponding to the fixed code stored in the initializing code storage section 16, and it is thereby possible to make operation timing of the signal processing section 15 of the image pickup apparatus 1 appropriately synchronize with operation timing of the signal processing section 27 of the CCU 2.

As described above, according to the present embodiment, bit values are inverted so that the ratio of bit values of 0 and 1 in data of a light-shielded pixel or saturated pixel out of digital data of an image acquired by image pickup of an object becomes a predetermined ratio. Therefore, according to the present embodiment, when digital data of the image acquired by image pickup of an object is serially transmitted using a differential transmission scheme, it is possible to secure transmission quality while suppressing increases in the amount of communication.

Note that according to the present embodiment, when 12-bit data is generated as one pixel worth of data, the bit value conversion section 15*a* and the bit value reconstituting section 27*b* may carry out the following processing or the like as a modification example.

The bit value conversion section 15*a* applies processing using predetermined table data to the 12-bit data corresponding to one pixel determined to be a light-shielded pixel or saturated pixel to thereby generate 16-bit data so that the ratio of bit values of 0 and 1 becomes 1:1.

FIG. 5 is a diagram illustrating an example of table data used in the processing according to a modification example of the present embodiment.

To be more specific, the bit value conversion section 15*a* divides (12-bit) data of a light-shielded pixel or saturated pixel into 3-bit portions from the beginning and converts the each data of the four portions obtained to 4-bit data using the table data in FIG. 5.

However, when the data divided into 3-bit portions in the aforementioned processing is any one of "000" and "111," the bit value conversion section 15*a* converts the data to 4-bit data while alternately switching between patterns (A) and (B) of the table data in FIG. 5.

To be more specific, when 12-bit data is divided, for example, into four 3-bit portions of "000," "000," "111" and "000" from the beginning, the bit value conversion section 15*a* converts the data of the four portions to 4-bit data so as to be "0100" (pattern (A)), "1011" (pattern (B)), "0010" (pattern (A)) and "1011" (pattern (B)). Furthermore, when 12-bit data is divided, for example, into four 3-bit portions of "000," "000," "111" and "010" from the beginning, the bit value conversion section 15*a* converts the data of the four portions to 4-bit data so as to be "0100" (pattern (A)), "1011" (pattern (B)), "0010" (pattern (A)) and "0101" (no pattern).

The bit value reconstituting section 27*b* then converts the 16-bit data of the light-shielded pixel or saturated pixel out of the data per pixel included in the parallel data obtained through the processing in the parallel conversion section 27*a* to 12-bit data using the same table data as that of the bit value conversion section 15*a* and thereby reconstitutes the data before being transmitted from the transmission circuit 17.

Note that when converting the 12-bit data of the light-shielded pixel or saturated pixel to 16-bit data so that the ratio of bit values of 0 and 1 becomes 1:1, the bit value conversion section 15*a* is not limited to the one which may perform the aforementioned processing but may be one which performs such processing as to divide, for example, the 12-bit data into 6-bit portions from the beginning, apply other table data to the data of the two portions obtained and thereby convert the data of two portions to 8-bit data.

According to the modification example of the present embodiment described above, it is possible to secure transmission quality when digital data of an image acquired by image pickup of an object is serially transmitted using a differential transmission scheme.

However, the present invention is not limited to the aforementioned respective embodiments, and it goes without saying that various modifications and applications can be made without departing from the spirit and scope of the invention.

What is claimed is:

1. An image pickup apparatus comprising:
    an image pickup section configured to acquire an image by image pickup of an object and acquire digital data of the image;
    a determining section that determines whether or not there are a predetermined number or more of consecutive bits with a first bit value or a second bit value in data per pixel included in the digital data acquired by the image pickup section;
    a bit value inversion processing section that applies, when a determination result that there are the predetermined number or more of consecutive bits with the first bit value or the second bit value is obtained from the determining section, processing of inverting the bit values so that a ratio between the first bit value and the second bit value included in the pixel data corresponding to the determination result becomes a predetermined ratio to the digital data acquired by the image pickup section; and
    a serial conversion section that serializes and outputs the respective bit values of the digital data obtained as the processing result of the bit value inversion processing section.

2. The image pickup apparatus according to claim 1, wherein the bit value inversion processing section performs processing of inverting bit values of data of a pixel corresponding to the determination result on a bit-by-bit basis.

3. The image pickup apparatus according to claim 1, wherein the predetermined ratio is 1:1.

4. An image pickup system comprising:
    an image pickup section configured to acquire an image by image pickup of an object and acquire digital data of the image;
    a determining section that determines whether or not there are a predetermined number or more of consecutive bits with a first bit value or a second bit value in data per pixel included in the digital data acquired by the image pickup section;
    a bit value inversion processing section that applies, when a determination result that there are the predetermined number or more of consecutive bits with the first bit value or the second bit value is obtained from the determining section, processing of inverting the bit values so that a ratio between the first bit value and the second bit value included in the pixel data corresponding to the determination result becomes a predetermined ratio to the digital data acquired by the image pickup section;
    a serial conversion section that serializes and outputs the respective bit values of the digital data obtained as the processing result of the bit value inversion processing section;
    a digital data transmission section that transmits the digital data serialized by the serial conversion section;
    a digital data reception section that receives the digital data transmitted from the digital data transmission section;
    a parallel conversion section that converts the digital data received from the digital data reception section to parallel data; and
    a bit value re-inversion processing section that applies, when a determination result that there are the predetermined number or more of consecutive bits with the first bit value or the second bit value is obtained from the determining section, processing of re-inverting the respective bit values inverted by the processing in the bit value inversion processing section to the parallel data obtained as the conversion result in the parallel conversion section.

5. The image pickup system according to claim 4, wherein the bit value inversion processing section performs processing of inverting bit values of data of a pixel corresponding to the determination result on a bit-by-bit basis.

6. The image pickup system according to claim 4, wherein the predetermined ratio is 1:1.

* * * * *